United States Patent
Losada-Pérez et al.

(10) Patent No.: US 10,705,083 B2
(45) Date of Patent: Jul. 7, 2020

(54) BIOPARTICLE CHARACTERIZATION AND IDENTIFICATION USING INTERFACE THERMAL RESISTANCE MEASUREMENT DURING BIOPARTICLE ADHESION AND DETACHMENT

(71) Applicants: IMEC VZW, Leuven (BE); Universiteit Hasselt, Hasselt (BE)

(72) Inventors: Patricia Losada-Pérez, Hasselt (BE); Derick Yongabi, Hasselt (BE); Mehran Khorshid, Hasselt (BE); Ward De Ceuninck, Tongeren (BE); Ronald Thoelen, Zonhoven (BE); Patrick Wagner, Everberg (BE)

(73) Assignee: IMEC VZW, Leuven (BE)

( * ) Notice: Subject to any disclaimer, the term of this patent is extended or adjusted under 35 U.S.C. 154(b) by 234 days.

(21) Appl. No.: 15/814,026

(22) Filed: Nov. 15, 2017

(65) Prior Publication Data

US 2018/0180609 A1    Jun. 28, 2018

(30) Foreign Application Priority Data

Dec. 27, 2016   (EP) .................................. 16206951

(51) Int. Cl.
*G01N 33/557* (2006.01)
*G01N 25/18* (2006.01)
(Continued)

(52) U.S. Cl.
CPC .......... *G01N 33/557* (2013.01); *G01N 25/18* (2013.01); *G01N 33/487* (2013.01);
(Continued)

(58) Field of Classification Search
CPC .... G01N 25/18; G01N 33/543; G01N 33/569; G01N 33/68; G01N 33/557
(Continued)

(56) References Cited

U.S. PATENT DOCUMENTS

2008/0280776 A1* 11/2008 Bashir .................. G01N 27/127
                                                                506/9
2010/0120163 A1*  5/2010 Larson .................. G01K 17/00
                                                                436/147
(Continued)

FOREIGN PATENT DOCUMENTS

EP      2 772 753 A1    9/2014
WO    03/100427 A1    12/2003

OTHER PUBLICATIONS

Peitzsch, M. et al, Chemical Engineering and Processing 2008, 47, 1000-1006.*

(Continued)

*Primary Examiner* — Arlen Soderquist
(74) *Attorney, Agent, or Firm* — McDonnell Boehnen Hulbert & Berghoff LLP

(57) ABSTRACT

The present disclosure relates to a method for characterizing and identifying a bioparticle. The method comprises introducing the sample to a substrate having a surface comprising a plurality of binding sites whereon bioparticles can be bound, determining, for at least one temperature, data representative for the interface thermal resistance of the surface of the substrate sufficiently long to include the detachment process of the bioparticles, and deriving, for the at least one temperature, a bioparticle retention time and/or detachment rate from the data representative for the interface thermal resistance data. The present disclosure also relates to a bio-sensing device suitable for the detection and/or characterization of target bioparticles.

20 Claims, 4 Drawing Sheets

(51) Int. Cl.
- G01N 33/543 (2006.01)
- G01N 33/569 (2006.01)
- G01N 33/68 (2006.01)
- G01N 33/487 (2006.01)

(52) U.S. Cl.
CPC ..... *G01N 33/54313* (2013.01); *G01N 33/569* (2013.01); *G01N 33/68* (2013.01); *G01N 2600/00* (2013.01)

(58) Field of Classification Search
USPC .................................................. 436/63, 147
See application file for complete search history.

(56) References Cited

U.S. PATENT DOCUMENTS

| | | | |
|---|---|---|---|
| 2010/0330578 A1* | 12/2010 | Duhr | B01L 3/50273 435/6.11 |
| 2012/0100636 A1* | 4/2012 | Johal | G01N 33/54373 436/501 |
| 2014/0242605 A1* | 8/2014 | Eersels | G01N 25/18 435/7.1 |

OTHER PUBLICATIONS

Chen, W. et al, Cellular and Molecular Bioengineering 2008, 1, 276-288.*
Guo, D. et al, British Journal of Pharmacology 2012, 166, 1846-1859.*
Vauquelin, G., Medicinal Chemistry Communication 2012, 3, 645-651.*
Van Grinsven, B. et al, ACS Nano 2012, 6, 2712-2721.*
Fang, Y., Expert Opinion on Drug Discovery 2012, 7, 969-988.*
Eersels, K. et al, ACS Applied Materials & Interfaces 2013, 5, 7258-7267.*
Bers, K. et al, Langmuir 2014, 30, 3631-3639.*
Wackers, G. et al, Sensors 2014, 14, 11016-11030.*
Cornelis, P. et al, Diamond & Related Materials 2014, 48, 32-36.*
Van Grinsven, B. et al, ACS Applied Materials & Interfaces 2014, 6, 13309-13318.*
Eersels, K. et al, Langmuir 2015, 31, 2043-2050.*
Li, W. et al, Journal of the American Chemical Society 2015, 137, 8199-8205.*
Cozens-Roberts, C. et al, Biophysical Journal 1990, 58, 107-125.*
Li, W. et al, Angewandte Chemie International Edition 2013, 52, 6726-6730.*
European Search Report, European Patent Application No. 16206951.2, dated Jun. 2, 2017, pp. 9 pages.
Hoffmann, C. et al., "Ligand Residence Time at G-Protein-Coupled Receptors-Why We Should Take Our Time to Study It", Molecular Pharmacology, vol. 88, No. 3, Jul. 7, 2015, pp. 552-560.
Lee, Donald et al., "Studying X31 Influenza Membrane Binding and Fusion Using Stochastic Assays and Simulations", Biophysical Journal, vol. 102, No. 3, Feb. 28, 2012, pp. 500a.
Meyners, Christian et al., "Kinetic Method for the Large-Scale Analysis of the Binding Mechanism of Histone Deacetylase Inhibitors", Analytical Biochemistry, vol. 460, Jun. 2, 2014, pp. 39-46.
Kiessling, Tobias R. et al., "Thermorheology of Living Cells-Impact of Temperature Variations on Cell Mechanics", New Journal of Physics, vol. 15, 2013, 045026, pp. 1-19.
Bonetta, Laura, "Flow Cytometry Smaller and Better", Nature Methods, vol. 2, No. 10, Oct. 2005, pp. 785-795.
Riethdorf, Sabine et al., Detection of Circulating Tumor Cells in Peripheral Blood of Patients With Metastatic Breast Cancer: A Validation Study of the CellSearch System, Clin. Cancer Res., 13(3), Feb. 1, 2007, pp. 920-928.
Law, Jodi Woan-Fei et al., "Rapid Methods for the Detection of Foodborne Bacterial Pathogens: Principles, Applications, Advantages and Limitations", Frontiers in Microbiology, vol. 5, Article 770, Jan. 2015, pp. 1-19.
Vercruysse, Dries et al., "Three-Part Differential of Unlabeled Leukocytes With a Compact Lens-Free Imaging Flow Cytometer", Lab-on-a-Chip, vol. 15, 2015, pp. 1123-1132.

\* cited by examiner

BIOPARTICLE CHARACTERIZATION AND IDENTIFICATION USING INTERFACE THERMAL RESISTANCE MEASUREMENT DURING BIOPARTICLE ADHESION AND DETACHMENT

CROSS-REFERENCE TO RELATED APPLICATIONS

The present application is a non-provisional patent application claiming priority to European Patent Application No. 16206951.2, filed Dec. 27, 2016, the contents of which are hereby incorporated by reference.

FIELD OF THE DISCLOSURE

The disclosure relates to the field of characterizing bioparticles. More specifically it relates to devices and methods for identifying bioparticles, such as cells with high selectivity and with low detection limit.

BACKGROUND

In many types of cancer, e.g., breast cancer, cells are released from the primary tumor and circulate in the blood stream until they lodge elsewhere in the body. The detection and identification of these circulating tumor cells (CNT's) is of major importance for an early diagnosis, for avoiding metastases, and for the follow-up of therapies. Early stage cancer detection is a milestone in cancer diagnosis and has triggered a plethora of studies with the aim to increase selectivity and reduce the limit of detection. To date, the available techniques for early cancer diagnosis using blood or liquid biopsies are often based on fluorescently-activated cell sorting (FACS, requiring fluorescent cell-labeling). This technique is time consuming and requires expensive instrumentation operated by specialized staff. Other techniques are also known.

One example of a technique that can be used is thermos rheology, as for example described by T. R. Kiessling in New Journal of Physics 15 (2013) art. No. 045026. The technique provides information on the mechanical properties of cells upon environmental changes but fluorescent labels are needed and it requires laborious optical imaging and data processing.

In another technique, use is made of fluorescence assisted cell sorting, as for example described by L. Bonetta in Nature Methods 2 (2005) 785-795. The technique has a high specificity and allows a very low detection limit, but fluorescent labels are required. In addition, cells need to be suspended such that information on tissue and cell-cell interactions are unavailable as well as the data processing is complicated due to the massive amounts of data that are obtained.

Yet another known technique for detecting certain types of cells is using a compact lens-free imaging flow cytometer, as for example described in Vercruysse et al. in Lab on a Chip 15 (2015) 1123-1132. In this setup, a lens-free imaging system is used for imaging cells in a flow cytometer. This technique is label-free, requires small volumes, is sensitive to cell morphology, and has the potential for further miniaturization. Nevertheless, using holographic images as is done in this technique results in a low resolution and the post analysis of the images is complex.

In addition, a method for identifying circulatory tumor cells (CTCs) in blood samples has been developed. This techniques, referred to as the CellSearch™ is described by Riethdorf, Sabine, et al., in Clinical Cancer Research 13.3 (2007): 920-928. The CellSearch™ uses protein-coated magnetic beads, which bind to cancer cells. The cells then are separated from the sample by applying a magnetic field to the mixture before being subjected to further analysis. This technique involves fluorescent staining the candidate cells and labelling the magnetic beads, thus, making the technique both laborious and expensive.

Also, molecular methods are used for the detection of cells, especially pathogens. These methods, reviewed in Law, Jodi Woan-Fei, et al in Frontiers in microbiology 5 (2015): 770 are based polymerase chain reactions oligonucleotide DNA microarrays, fluorescent in situ hybridization, and pyrosequencing. However, these techniques lack specificity and require target enrichment prior to detection. Unfortunately, common enrichment techniques suffer from cell loss, sample contamination and/or require laborious labelling steps. Moreover, these techniques are time inefficient and require highly skilled staff, as well as bulky and expensive instrumentation.

There is still a need for better methods and devices for characterizing or identifying bioparticles, such as for example cells or cell types.

SUMMARY

The present disclosure provides methods and devices for identifying bioparticles, such as cells or cell types, at low concentrations, for example, in body fluids, beverages, liquefied food samples, environmental samples, and buffer solutions. In example embodiments, identification of cells without using labelling or staining agents or cell-type specific antibodies is provided.

The present disclosure relates to a method for characterizing a bioparticle, the method comprising: introducing the sample to a substrate having a surface comprising a plurality of binding sites whereon bioparticles can be bound, determining, for at least one temperature, data representative for the interface thermal resistance of the surface of the substrate sufficiently long to include the detachment process of the bioparticles, and deriving, for the at least one temperature, a bioparticle retention time and/or detachment rate from the data representative for the interface thermal resistance data.

In example embodiments, a method is provided that label free detection can be obtained. Furthermore, no staining agents or cell-type specific antibodies need to be used. In addition, in example embodiments, a method is provided that is low-cost, fact, user-friendly and can be applied to bioparticles such as cells at low concentrations in samples. The substrate may be a structured substrate and the binding sites may be binding cavities in which bioparticles can be bound.

Determining data representative for thermal resistance data may be performed for a plurality of temperatures and deriving a bioparticle retention time and/or detachment rate from the thermal resistance data comprises determining bioparticle retention time and/or detachment rate as function of temperature.

In some embodiments, even a more accurate detection can be obtained based on the temperature dependency of the retention time and/or detachment rate of the particles under study.

Determining data representative for thermal resistance data may comprise providing a heating power using a power at a first side of the structured substrate and sensing at least a temperature at the first side of the substrate and at a second side, opposite to the first side with respect to the substrate.

The method may comprise obtaining a substrate having a surface comprising a plurality of binding cavities in which the target bioparticle can be bound.

The method further may comprise, prior to the recording and the deriving, rinsing the substrate with a fluid.

The method may comprise providing a sample fluid in contact with the surface comprising the plurality of binding sites and/or wherein the obtaining a substrate comprises binding the target bioparticles to the surface comprising the plurality of binding sites.

The present disclosure also relates to a bio-sensing device suitable for the detection and/or characterization of target bioparticles, the bio-sensing device comprising:

a heating element for heating using a power, a sample holder comprising a substrate having a surface comprising a plurality of binding sites to which target bioparticles can bind, the sample holder further being adapted for exposing the substrate at one side to the heating element, a first temperature sensing element for sensing a temperature at the side where the substrate can be exposed to the heating element and a second temperature sensing element for sensing a temperature at the side opposite thereto with respect to the substrate, a processing means programmed for determining, for at least one temperature, data representative for thermal resistance data based on temperature values obtained with the first temperature sensing element and the second temperature sensing element and the power for the heating element, the processing means furthermore being programmed for deriving, for at least the one temperature, a bioparticle retention time from the thermal resistance data.

The processing means may be programmed for calculating data representative of thermal resistance data as function of temperature and for deriving bioparticle retention time as function of temperature.

The substrate may be an imprinted substrate.

The substrate may be a polymer.

The biosensing device may be adapted for characterizing target bioparticles with an average diameter of D, and wherein the binding cavities in the substrate have an average diameter in the range 1.5 times D to 0.5 times D.

The binding cavities in the substrate may have an average diameter in the range 0.1 nm to 100 µm. The structured substrate may be a surface imprinted substrate or a molecularly imprinted substrate. The surface of the binding cavities may be functionalized for specific binding of the particles.

The biosensing device may comprise, at a side of the structured substrate opposite to the thermal element, a fluid compartment for exposing that side of the structured substrate to a fluid, the second temperature sensing element being positioned in the fluid compartment.

The processing means may be adapted for outputting, based on the obtained bioparticle retention time, a characteristic of the target bioparticles.

The heating element may be controlled by a power resistor providing an input power. The first temperature sensing element and/or the second temperature sensing element may be a thermocouple. The biosensing device may comprise a controller for controlling the heating element and for controlling the temperature sensing elements for obtaining input power and temperature values for different temperatures as sensed with the first temperature sensing element.

The present disclosure also relates to a controller being programmed for performing a method as described above.

The present disclosure also relates to a computer program product comprising instructions which, when executed on a processing means, induce a method as described above.

The present disclosure also relates to a diagnostic device comprising a biosensing device as described above, the diagnostic device furthermore being adapted for deriving based on a characterization of a bioparticle pathology of an object.

Particular aspects of the disclosure are set out in the accompanying independent and dependent claims. Features from the dependent claims may be combined with features of the independent claims and with features of other dependent claims as appropriate and not merely as explicitly set out in the claims.

These and other aspects of the disclosure will be apparent from and elucidated with reference to the embodiment(s) described hereinafter.

BRIEF DESCRIPTION OF THE FIGURES

The above, as well as additional, features will be better understood through the following illustrative and non-limiting detailed description of example embodiments, with reference to the appended drawings.

Figure 1:
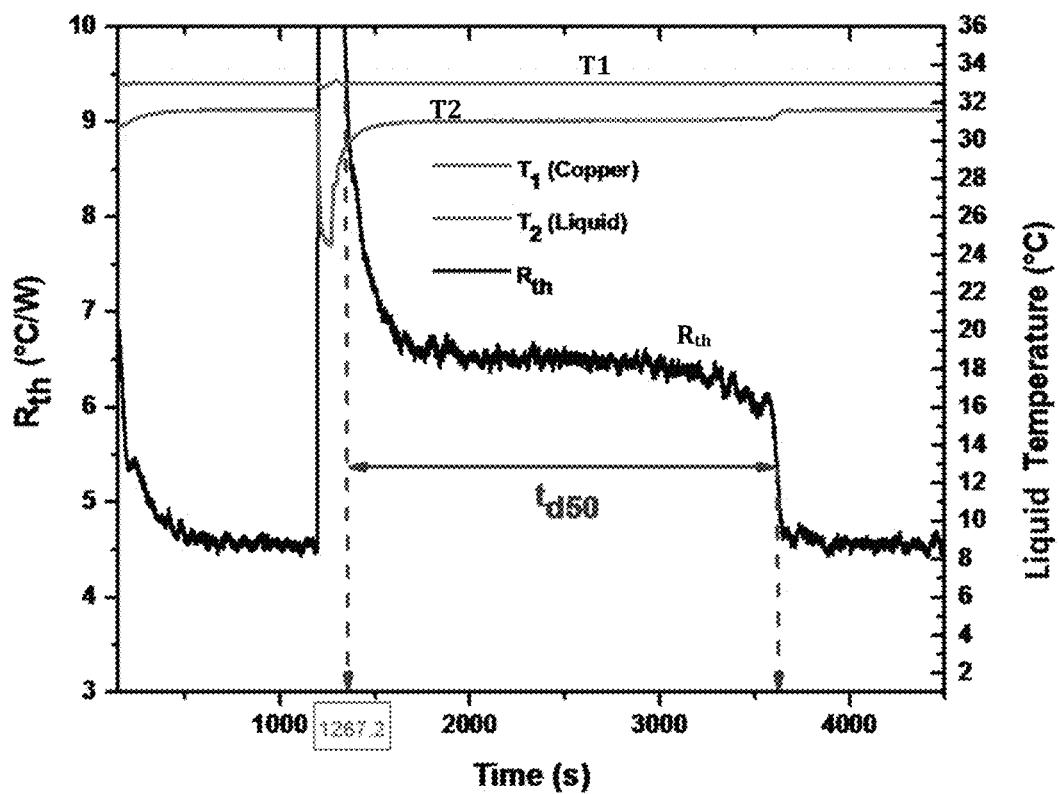
FIG. 1 illustrates the cell-detachment time td50, according to an example embodiment.
Figure 2:
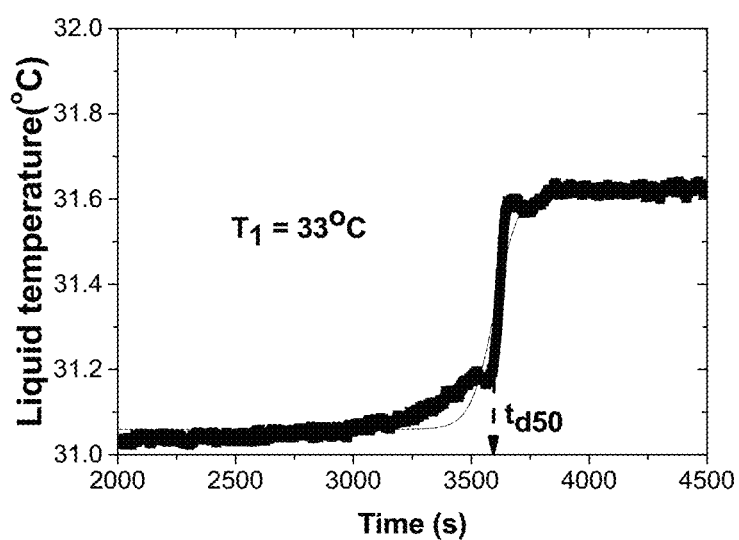
FIG. 2 illustrates the use of liquid temperature analysis, according to an example embodiment.

Any reference signs in the claims shall not be construed as limiting the scope.

In the different drawings, the same reference signs refer to the same or analogous elements.

All the figures are schematic, not necessarily to scale, and generally only show parts which are necessary to elucidate example embodiments, wherein other parts may be omitted or merely suggested.

DETAILED DESCRIPTION

Example embodiments will now be described more fully hereinafter with reference to the accompanying drawings. That which is encompassed by the claims may, however, be embodied in many different forms and should not be construed as limited to the embodiments set forth herein; rather, these embodiments are provided by way of example. Furthermore, like numbers refer to the same or similar elements or components throughout.

The present disclosure will be described with respect to particular embodiments and with reference to certain drawings but the disclosure is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the disclosure.

The terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the disclosure described herein are capable of operation in other sequences than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present disclosure, the only relevant components of the device are A and B.

Reference throughout this specification to "one embodiment" or "an embodiment" means that a particular feature, structure or characteristic described in connection with the embodiment is included in at least one embodiment of the present disclosure. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the disclosure, various features of the disclosure are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed disclosure requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this disclosure.

Furthermore, while some embodiments described herein include some but not other features included in other embodiments, combinations of features of different embodiments are meant to be within the scope of the disclosure, and form different embodiments, as would be understood by those in the art. For example, in the following claims, any of the claimed embodiments can be used in any combination.

In the description provided herein, numerous specific details are set forth. However, it is understood that embodiments of the disclosure may be practiced without these specific details. In other instances, well-known methods, structures and techniques have not been shown in detail in order not to obscure an understanding of this description.

Where in embodiments of the present disclosure reference is made to a bioparticle, this is defined as a relatively small or the smallest discrete portion or amount of biological material. This encompasses, e.g., a cell or a molecule. Where reference is made to target bioparticles, reference is made to those particles targeted for characterizing using the present technique.

Where in embodiments according to the present disclosure reference is made to thermal resistance Rth, reference is made to the ratio of the temperature difference $\Delta T$ of the temperature at each side of the imprinted substrate comprising the target bioparticles to the input power P, i.e., $Rth=\Delta T/P$.

Where in embodiments of the present disclosure reference is made to cavity or binding cavity, reference is made to a hollow space or hole in a substrate wherein the target bioparticles can position themselves.

Where in embodiments of the present disclosure reference is made to a structured substrate, reference is made to a substrate that does not have a flat surface, but that has shallow or deep cavities in the surface.

In a first aspect, embodiments of the present disclosure relate to a method for characterizing a bioparticle. Typically in an application, the bioparticle may be a target bioparticle being a particle of interest, e.g., for testing whether certain bioparticles are present in a sample. According to embodiments of the present disclosure, the method comprises introducing the sample to a substrate having a surface comprising a plurality of binding sites to which bioparticles can be bound. The method furthermore comprises, for at least one substrate temperature, determining data representative for interface thermal resistance data of the surface of the substrate for a sufficiently long time to include the entire detachment process. The method also comprises deriving, for the at least one temperature, a bioparticle retention time from the data representative for the thermal resistance data. The data representative for thermal resistance data may be thermal resistance data or may be for example temperature data that, under known heating conditions, correspond with thermal resistance data. The substrate may be a structured substrate with binding cavities as binding sites.

According to some embodiments of the present disclosure, determination of data representative for the thermal resistance data may be performed for a plurality of temperatures and deriving a bioparticle retention time from the thermal resistance data may comprise determining bioparticle retention time as function of temperature for predetermined substrate and medium conditions.

It was surprisingly found that there was a release of the bioparticles after a certain retention time, allowing accurate characterization of the type of the bioparticle, e.g., cell. It thus was found that there is a characteristic and sharply defined retention time after which all cells bound on a SIP release collectively. The retention time is cell-type- and temperature dependent and this information can be used to estimate the adhesion energy, being in turn characteristic for the cell-type under study. It thereby is to be noted that the collective spontaneous release is unrelated to the cell cycle and the phenomenon occurs also with dead cells.

The bioparticle retention time, also referred to as the bioparticle detachment time, is determined as the time span describing the length of time for all, or a fraction of cells to remain attached. In some embodiments, for example a bioparticle retention time td50, is used, expressing the time span between the medium exchange, resulting in a sharp initial Rth peak, and the mid-point of the detachment process. It is the total time to detach 50% of the cells. The definition of detachment time here is a working definition. It includes any time used to describe the time span between cell adhesion and detachment. The cell detachment time td50 is illustrated in FIG. 1. Thus the retention time is the time span between the end of the injection of cells until the equilibrium Rth or medium temperature signal changes by 50%.

In embodiments of the present disclosure, the principle of detection and identification of different cells types by estimating their adhesion energy to synthetic receptors using a thermal transport method is thus exploited. A rough estimation of the energy required by the cells to detach was determined by multiplying the supplied heating power with the cell-detachment time (or retention time) td. The temperature-time correlation is considered as a fingerprint for each cell and can be related to the adhesion energy profile of the specific type of cell to its imprint.

Figure 3:
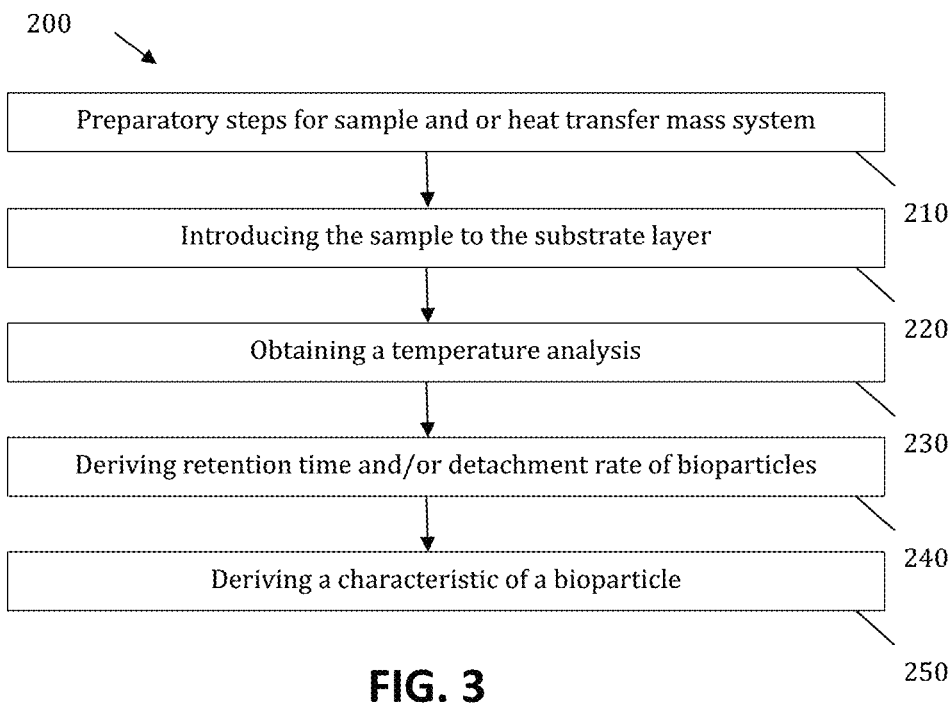
FIG. 3 illustrates a flow chart of a method, according to an example embodiment.

By way of illustration, embodiments of the present disclosure not being limited thereto, an example of a flowchart illustrating steps of an exemplary method for characterizing cells is shown in FIG. 3. The method can be easily applied using a device as will be described in the second aspect, although embodiments are not limited thereto.

In a first step 210 of the method 200, the sample as well as the device may undergo some preparatory steps 210, such as sample preparation, cleaning of the device, performing some calibration steps etc. Although such steps may result in more accurate results obtained by the method, such steps are not considered essential for performing methods according to embodiments of the present disclosure. The preparatory steps 210 may also include the step of obtaining a substrate.

Obtaining the substrate can be performed in a plurality of manners. The substrate may be previously made. The substrate has a surface comprising a plurality of binding sites to which bioparticles can be bound. In some embodiments obtaining the substrate may be obtaining an imprinted substrate and may comprise inserting or positioning or fixing the structured substrate on or in the sample holder. The latter may correspond with inserting of a sample imprinted substrate (as a cartridge) into a cartridge reader. In an example embodiment, the substrate is a surface imprinted substrate such as a surface imprinted polymer. In a first step, the surface imprinted polymer may be fabricated by polymerizing a Polyurethane mixture up to the gelling point. The Polyurethane gel is then diluted and spincoated on a transducer (e.g., a metal substrate). In a second step, template cells are spincoated on a PDMS stamp. In a third step, the PDMS stamp is pressed into the polyurethane layer. In a fourth step, the template cells and the stamp are removed, the layer can now specifically rebind a target cell.

In one embodiment of the disclosure, the substrate is a molecularly imprinted substrate such as a molecularly imprinted polymer. In a first sub-step a polymerizing template with functional monomers in a cross-linked matrix, in a second sub-step the template is extracted. In a third sub-step, binding cavities (micro/nanocavities) are obtained which can specifically rebind the target.

In a second step, the method 200 comprises the step of introducing 220 the sample to a substrate having a surface comprising a plurality of binding sites to which bioparticles can be bound. Stated differently, the sample is introduced to the substrate layer. By doing so, bioparticles will bind to the sites, e.g., for a structured substrate with binding cavities the bioparticles will bind in the binding cavities of the structured substrate. According to embodiments of the present disclosure, this introducing step is applied sufficiently long such that not only the binding of the particles at the binding sites is performed but also that detachment and detachment rate of the bioparticles from the binding cavities can be monitored. According to at least some embodiments of the disclosure, before providing a heating power, the structured substrate is rinsed with a fluid. The forces exerted by the liquid flow are sufficient to break non-specific sticking between target bioparticle and binding cavities, which match only in size while missing chemical complementarities, therefore being less or not accurately bound. Bioparticles other than target bioparticles, which are only weakly and non-specifically bound are released from the substrate by rinsing while the target bioparticles remain sticking to the binding sites of the substrate. In an example embodiment, the step of rinsing before providing a heating power enhances the selectivity of the target bioparticle detection. According to some embodiments of the disclosure, PBS can be used as rinsing fluid.

In a third step, the method 200 comprises determining 230 data representative for thermal resistance data of the surface of the substrate for at least one substrate temperature, whereby the determining occurs sufficiently long to record data not only the moment of binding of the bioparticles in the binding cavities but also the moment and the entire process of detachment of the bioparticles from the binding sites. Determining data representative for thermal resistance data typically may comprise providing a heating power using a power at a first side of the substrate. The latter results in a temperature gradient being present over the substrate and thus—when bound in the binding cavities—over the target bioparticles to be characterized and/or detected. The determination of data representative for the thermal resistance also typically comprises sensing at least a temperature at the first side of the biocompatible substrate and at a second side, opposite to the first side with respect to the substrate. From these measurements and the power for the heating element used, according to embodiments of the present disclosure, at least one thermal resistance value can be calculated. By way of example, a Savitsky-Golay filter could be used for the processing of the data, although embodiments of the present disclosure are not limited thereto. It is to be noticed that systems may be programmed for using, for a given power, temperature data as representative for interface thermal resistance data, such that during use the interface thermal resistance data are not explicitly calculated but use is made of temperature data and of the correspondence between the temperature data and the interface thermal resistance data for a given power applied.

In some embodiments, calculating at least one thermal resistance value comprises determining the thermal resistance as function of temperature, i.e., determining different thermal resistance values at different temperatures. The calculating may furthermore include applying a filter for improving the signal to noise ratio. The temperature used as reference can in principle be chosen and may for example be the temperature sensed with the first temperature sensing element.

In yet a further step, the method 200 comprises deriving a bioparticle retention time 240 and/or detachment rate from the thermal resistance. In some embodiments, a retention time and/or detachment rate of the bioparticles as function of temperature is obtained. The retention time and/or detachment rate or the retention time and/or detachment rate as function of temperature may be used as a fingerprint for characterizing the bioparticle in the sample that is studied (i.e., deriving a characteristic of a bioparticle 250).

Further optional steps of the method according to embodiments of the present disclosure may express the functionality of components described in the second aspect, or may correspond with features as described in the example below.

Figure 4A:
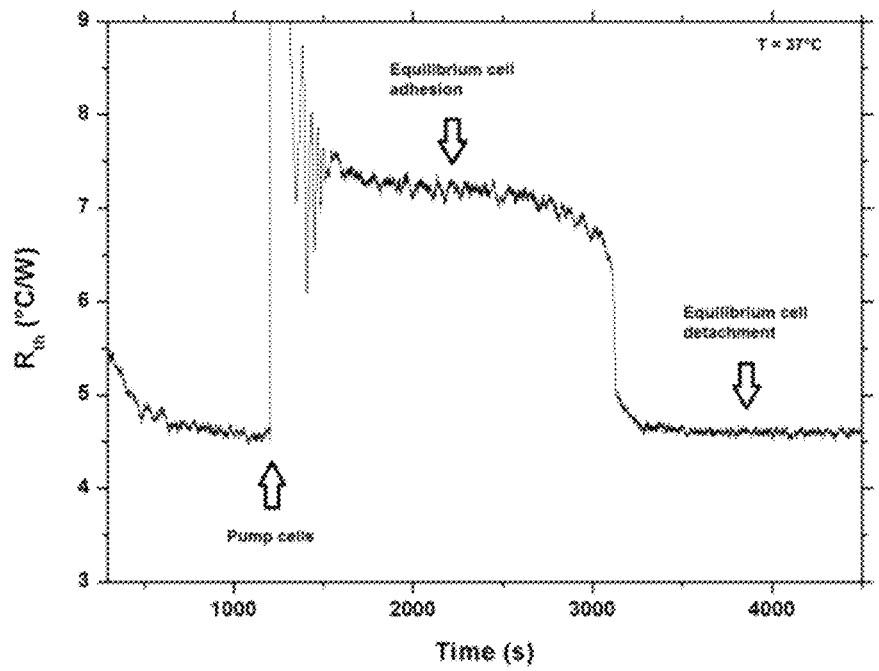
FIG. 4a and FIG. 4b illustrate the heat transfer resistance response showing spontaneous detachment of bound yeast cells (FIG. 4a) and ZR-75 breast-cancer cells from the SIP layer (FIG. 4b), according to an example embodiment.
Figure 4B:
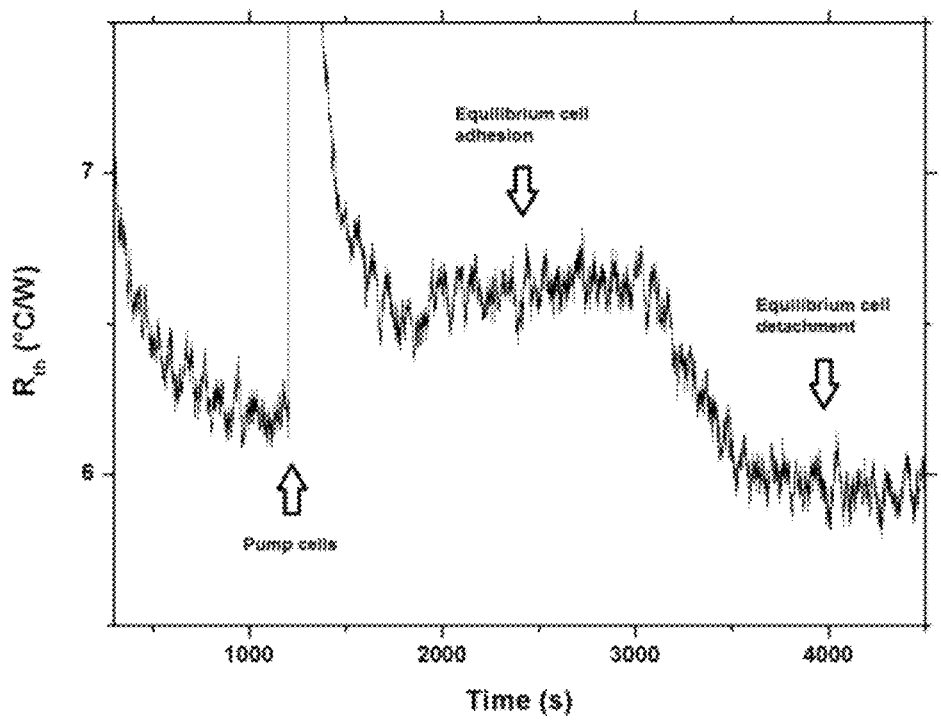

An example of the time dependence of the stability of cells-SIP adhesion is illustrated in FIG. 4a for yeast cells. Upon addition of yeast cells, an increase of Rth by 2.5° C./W was observed indicating cell binding to the imprinted chip consisting of a thin polyurethane layer on aluminum. After 45 min, a slow decrease in the Rth signal is observed followed by a sharp drop, after which the initial baseline of Rth prior to cell addition is recovered. In FIG. 4b, the thermal resistance Rth response at 37° C. chip temperature is shown, indicating spontaneous detachment of bound yeast cells (FIG. 4a) and ZR-75 breast-cancer cells from the SIP layer (FIG. 4b).

Figure 5:
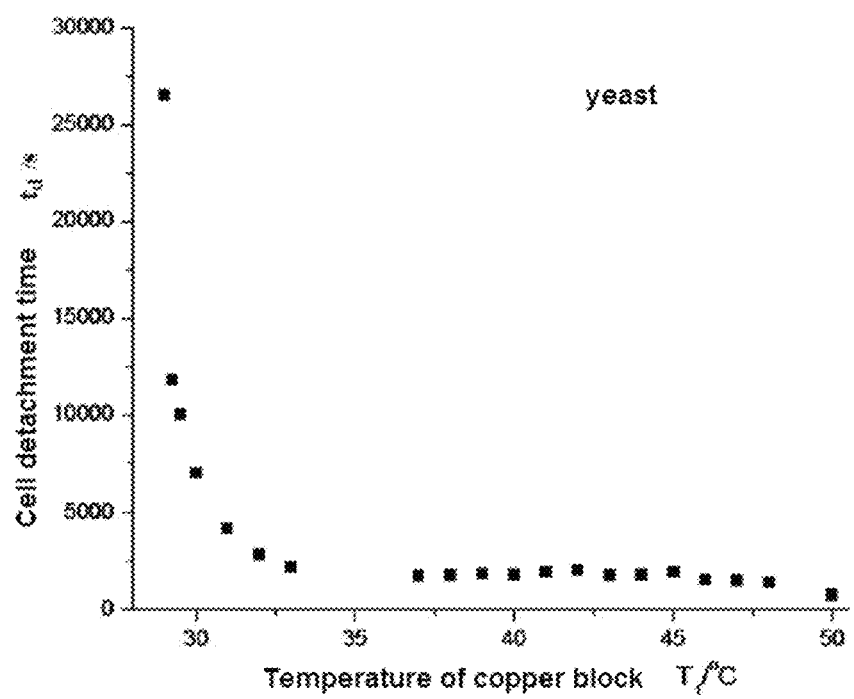
FIG. 5 illustrates the cell retention time td50 as function of the temperature measured at the SIP sensor chip, according to an example embodiment.

By way of illustration, an example of a curve illustrating cell retention time td for yeast as a function of the temperature measured at the backside of the SIP sensor chip is shown in FIG. 5. The temperature-time correlation is considered as a fingerprint for the cell type and can be related to the adhesion energy profile of the specific type of cell to its imprint.

In a second aspect, the preset disclosure relates to a biosensing device suitable for the characterization of target bioparticles. According to embodiments of the present disclosure, the bio-sensing device comprising a heating element for heating using a power and a sample holder comprising a substrate having a surface comprising a plurality of binding sites to which target bioparticles can bind, the sample holder further being adapted for exposing the substrate at one side to the heating element. The device also comprises a first temperature sensing element for sensing a temperature at the side where the substrate can be exposed to the heating element and a second temperature sensing element for sensing a temperature at the side opposite thereto with respect to the substrate. The temperature information thereby is recorded sufficiently long to include the moment of detachment of the bioparticles. According to embodiments of the present disclosure, the device also comprises a processing means programmed for determining data representative for thermal resistance value based on temperature values obtained with the first temperature sensing element and the second temperature sensing element and the power for the heating element. The processing means furthermore is programmed for deriving, for the at least one temperature, a bioparticle retention time from the thermal resistance data. According to some embodiments of the present disclosure, recording of thermal resistance data may be performed for a plurality of temperatures and deriving a bioparticle retention time and/or detachment rate from the thermal resistance data may comprise determining bioparticle retention time and/or detachment rate as function of temperature.

Figure 6:
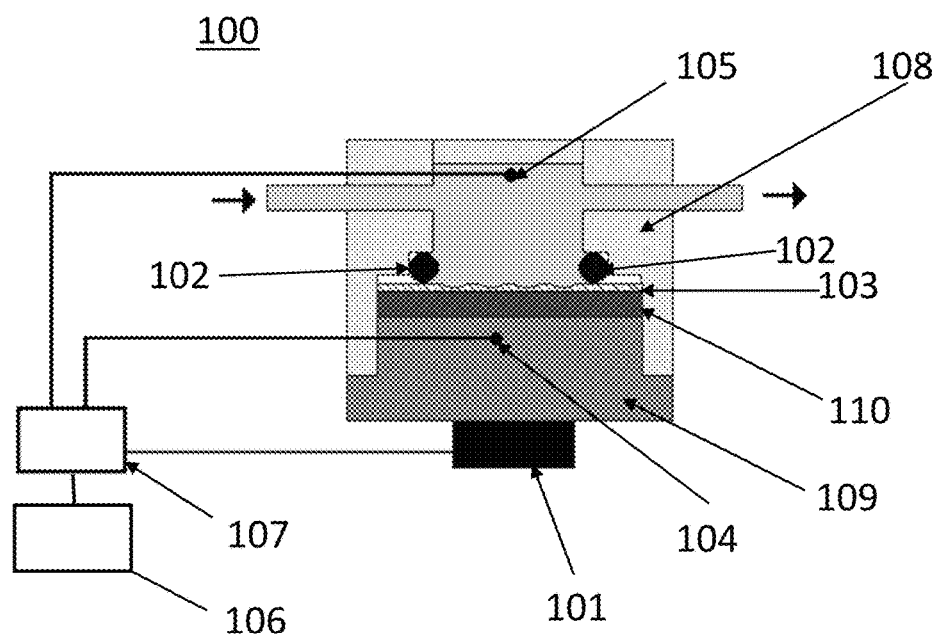
FIG. 6 shows a heat transfer mass device with a polymer surface, including especially surface-imprinted polymer layers acting as the receptor for specific cell detection, according to an example embodiment.

By way of illustration, embodiments of the present disclosure not limited thereto, a schematic overview of standard and optional components is shown in FIG. 6. According to embodiments of the present disclosure, the bio-sensing device 100 comprises a heating element 101. Such a heating element 101 may in one example be a block of solid material and a heating element, e.g., a power resistor providing an input power. In principle, any type of heating element may be used. The heating element according to embodiments typically is adapted—e.g., in relative position with respect to the sample or sample-substrate—so that a temperature gradient is created over the sample or sample-substrate. Heating elements thus may be used that provide a heating source at one side of the sample or sample-substrate, which transfers through the sample, and then goes into the fluid positioned at the opposite side of the sample or sample-substrate (i.e., opposite to the heating element, with reference to the substrate.

The biosensor 100 furthermore comprises a sample holder 102. The sample holder 102 according to embodiments of the present disclosure comprises a substrate 103 having a surface comprising a plurality of binding sites to which target bioparticles can bind. Such a structured substrate may for example be a substrate having a plurality of binding cavities in which target bioparticles can bind, such as an imprinted substrate, although embodiments of the present disclosure are not limited thereto and, e.g., a structured substrate based on laser ablation of cavities also can be used. The sample holder 102 furthermore is adapted for exposing the substrate at one side to the heating element.

The device 100 furthermore comprises a first temperature sensing element 104 for sensing a temperature at the side where the substrate 103 can be exposed to the heating element 101 and a second temperature sensing element 105 for sensing a temperature at the side opposite thereto with respect to the substrate 103. Such temperature sensing elements 104, 105 can be any type of temperature sensing elements 104, 105, one example being a thermocouple. The device 100 also may comprise more than two sensing elements, such as for example an array of temperature sensing elements, although for operating embodiments of the disclosure, two temperature sensing elements are sufficient.

According to embodiments of the disclosure, the heating element 101 is in direct contact with a metal block 109 which is in direct contact with a metal carrier 110. Heat produced by the heating element 101 is transferred to the substrate 103 through the metal block 109 and the metal carrier 110. In a particular embodiment of the disclosure, the metal block 109 is a copper block. In a particular embodiment of the disclosure, the metal carrier 109 is an aluminum block.

According to an embodiment of the disclosure, the substrate 103 is a substrate layer deposited on the metal carrier 110. In a particular embodiment of the disclosure, the substrate 103 is a thin layer of polymer material, e.g., a thin layer of polyurethane. The thickness of such a layer may for example be one or a few micrometer. In an example embodiment, this may be for example about 1.2 µm.

According to some embodiments of the present disclosure, the substrate 103 may be an imprinted substrate 103. Such an imprinted substrate may be a surface imprinted polymer (SIP). The device may then be especially suitable for detecting and/or characterizing biological cells, although embodiments are not limited thereto. In an example embodiment, the biosensing device 100 may be used to differentiate between biological cells by slight differences in shape, size, and functionalities in functional groups on their surface.

The surface may have cavities of which the diameter is adapted to the average size of the particles envisaged for detection with the sensing device. For cell imprinted polymer layers, the average diameter of the imprints may correspond with between 0.5 and 0.9 times the average diameter of the cell. For small molecules (MIPs) the imprinting cavities may be bigger than the target molecule.

The binding cavities in the substrate may have an average diameter in the range 0.1 nm to 100 µm, e.g., depending on the application and particles envisaged. For SIP's the average diameter may be in the range 1 µm to 100 µm, e.g., between 2 µm and 25 µm, such as between 3 µm and 22 µm. For the small molecules (MIPs) the average diameter may be between 0.1 nm and 100 nm.

In some embodiments, the synthetic receptors are surface-imprinted polymer (SIP) layers covered with imprints of different types of target cells: In the examples used, the breast-cancer cell lines MCF-7 and ZR-75, and yeast for comparison. The SIP layers were coupled to the 'HTM' transducer platform, which measures the heat-transfer resistance Rth of the solid-liquid interface.

According to some embodiments, the substrate 103 is a layer covered with receptors created by imprinting techniques, including molecular imprinting (MIP) and surface imprinting (SIP). When using a surface imprinted polymer, the biosensing device 100 may be especially suitable for detecting molecules, although embodiments of the present disclosure are not limited thereto. In an example embodiment, the biosensing device is able to perform fast and low-cost measurements in biological samples.

As indicated above, also other types of substrates 103 can be used, such as substrates structured using other types of imprinting, using laser ablation, by microspotting, by growing MIPs directly on the surface, by ion beam lithography, by ink-jetting, etc. In some embodiments the cavities furthermore are functionalized, so that the inner surface of the cavities is designed to attract and/or specifically bind bioparticles. Alternatively, the substrates are not structured but only functionalized. The functionalization may be performed using, e.g., functional groups, complementary groups, organisms or fractions thereof, etc.

The biosensing device 100 furthermore comprises a processing means 106 programmed for calculating at least one thermal resistance value based on temperature values obtained with the first temperature sensing element 104 and the second temperature sensing element 105 and an input power for the heating element 101. The processing means furthermore is programmed for deriving, for the at least one temperature, a bioparticle retention time and/or detachment rate from the thermal resistance data. In some embodiments the processing means is adapted for obtaining a bioparticle retention time and detachment rate as function of temperature.

According to example embodiments, the processing means 106 is programmed for using the bioparticle retention time for deriving a characteristic of the target bioparticles from the bioparticle retention time. In example embodiments, the processor or processing means 106 is adapted for deriving a characteristic of the target bioparticles, such as for example a type of bioparticle such as a cell type, from the bioparticle retention time as function of temperature. The processing means 106 furthermore may be adapted for filtering the data, to improve signal to noise ratio. The processing means 106 furthermore may be adapted for deriving from the processing means 106 may be adapted for taking into account experimental conditions, such as for example taking into account a heating rate or taking into account a position bioparticles with respect to the heating element (i.e., the bioparticles being at the side of the heating element with respect to the remaining part of the biocompatible substrate or at the opposite side thereof). The processing means 106 may be programmed for performing the above in an automated way. Such processing means 106 may be a software-based processor, as well as a hardware-based processor. It may for example make use of a predetermined algorithm, a look up table, or a neural network for performing the processing.

According to some embodiments, the biosensing device 100 may comprise a fluid compartment 108 for exposing the surface of the substrate 103 side comprising binding sites to a fluid. The second temperature sensing element 105 being positioned in the fluid compartment 108. The fluid may be used for introducing the target bioparticles. The biosensing device 100 may comprise a flow cell comprising the fluid compartment 108 and furthermore comprising a pumping and/or valve device for transferring fluid from and to the fluid compartment 108. According to some particular embodiments, the flow cell may comprise a syringe device coupled to a Perspex flow cell with a suitable inner volume. The dimensions of the inner volume may be selected based on the final device goals. To set up a test device an example was shown having a suitable inner volume of around 110 µl. The effective area of the substrate surface depends on the dimensions of the flow cell and may be in one particular example of the order of around 28 $mm^2$ exposed to the liquid. In some embodiments, the electrode may be sealed with an O-ring. The operation of the biosensing device may be controlled by a controller 107. A controller 107 may control the heat element and the temperature sensing elements for obtaining input power and temperature values. Such values may be obtained for different input powers, or—corresponding therewith—for different temperatures as sensed with the first temperature sensing element.

The device also may be equipped with electrodes for measuring an impedance or with a transparent bottom for measuring a fluorescence signal, as the measurement principle can be easily combined with other measurement techniques, e.g., for cross-checking. Further optional features may be as described in the example below.

By way of illustration, embodiments of the present disclosure not being limited thereto, a heat transfer device with a surface imprinted polymer layer acting as receptor for specific cell detection can be seen in FIG. 5.

In a third aspect, the present disclosure also relates to a controller 107 adapted for controlling a heating element 101, temperature sensing elements 104, 105 and a processor 106 for performing a method according to embodiments of the first aspect. Such a controller 107 may be part of a device as described in the first aspect or may be suitable for communicating therewith. The controller 107 may be implemented as software—to be implemented on a processor—or may be implemented as hardware. The controller 107 may be implemented, such that after activation and obtaining the imprinted substrate, the sensing, calculating and where included the deriving step occurs in an automated and/or automatic way. The controller 107 may be programmed, e.g., it may include a microprocessor or an FPGA whereon a set of instructions are implemented. Alternatively, the controller 107 can be software based and thus may correspond with a computer program product. The present disclosure also relates to a computer program product providing, when run on a computer, the functionality of any of the methods as described in the second aspect. Such a computer program product may be carried on a data carrier, the disclosure thus also relating to a data carrier, such as a CD-ROM, a disk, a USB memory device, a DVD, a pc, or a work station. The computer program product may be stored in a machine readable form and/or may be transmitted over a network, e.g., local or wide area network.

By way of example, embodiments of the present disclosure not being limited thereto, the total provided energy required to detach three different types of cells from a surface-imprinted chip as calculated using a method according to an embodiment of the present disclosure. As discussed above, cells detach from their imprinted polymer layers at specific times depending on the set temperature of the copper block. In view of this observation combined with the initial hypothesis that for a given temperature, the detachment time of cells from their polymer imprinted layers depends on the type of cell, an experiment was designed towards developing a new diagnostic strategy. Three cell types; S. cerevisiae ($\approx 12\times 10^6$ cells/ml), MCF-7 ($1\times 10^6$ cells/ml) and ZR-75 ($1\times 10^6$ cells/ml) were exposed to their corresponding surface imprinted polymer layers in the heat transfer mass device. At a constant temperature of 37° C., the time-dependent liquid temperature was monitored for a period of one hour and the corresponding Rth response calculated. From the Rth response, the detachment time for each cell type was calculated. The detachment time for yeast cells was found to be approximately 24.2 minutes (1454 seconds) while MCF-7 cells took a shorter time of 19 minutes (1140 seconds). ZR-75 cells took the longest time to detach from the polymer layer with a detachment time of 29.4 minutes (1763 seconds). The results suggest that it is possible to detect cells based on their detachment times from SIP layers. Furthermore, MCF-7 and ZR-75 cells which are similar in size (about 20 μm) have a detachment time difference of 10.4 minutes. This time difference is way above noise levels such as the time taken for the Rth signal to stabilize back after a sudden temperature change (3±1 minutes which is fairly constant with temperature). Therefore, for measurements at the same temperature, a cell detachment time difference of more than 4 minutes is a reliable measure that allows to discriminating between cells.

Figure 7:
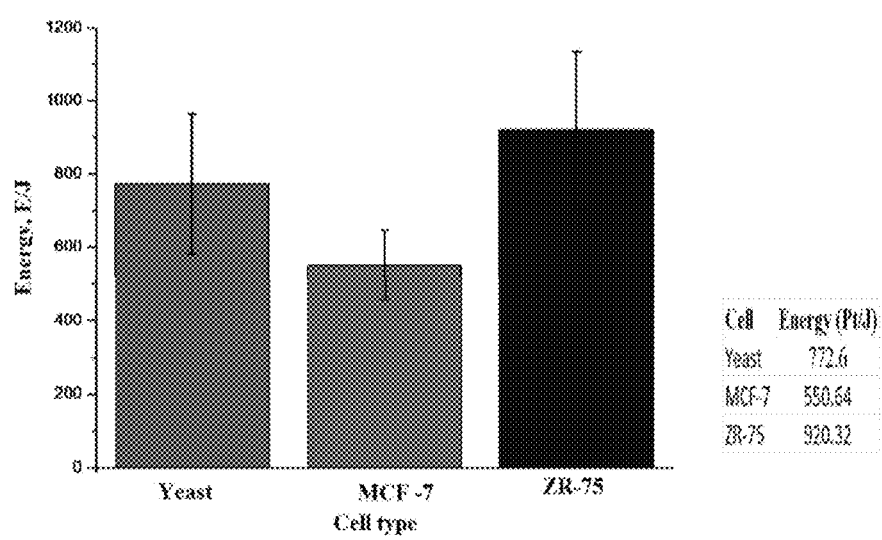
FIG. 7 shows the total provided energy required to detach three different types of cells from a surface-imprinted chip as calculated, as can be obtained according to an example embodiment. This energy analysis opens the possibility to characterize cells in terms of adhesion.

All data shown are for a chip temperature of 37° C. Despite the fact that these cells are very similar in size and shape, the proposed methodology allows to distinguish clear differences in interfacial properties of both ZR-75 and MCR-7 cells. As a matter of fact, the adhesion of ZR-75 is stronger than that of MCR-7, in agreement with a recent study on the metastatic capacity of cancer cells in relation to their adherence to endothelial cells. The calculated energy levels are shown in FIG. 7. It is to be noted that these are device-specific values and the energy value refers to all released cells together, not to an individual cell.

While some embodiments have been illustrated and described in detail in the appended drawings and the foregoing description, such illustration and description are to be considered illustrative and not restrictive. Other variations to the disclosed embodiments can be understood and effected in practicing the claims, from a study of the drawings, the disclosure, and the appended claims. The mere fact that certain measures or features are recited in mutually different dependent claims does not indicate that a combination of these measures or features cannot be used. Any reference signs in the claims should not be construed as limiting the scope.

What is claimed is:

1. A method for characterizing a bioparticle, the method comprising:
    introducing a sample to a substrate having a surface comprising a plurality of binding sites whereon bioparticles can be bound;
    determining, for at least one temperature, data representative of an interface thermal resistance of the surface of the substrate that includes equilibrium adhesion and equilibrium detachment data for the bioparticles; and
    deriving, for the at least one temperature, a bioparticle retention time and/or detachment rate from the data representative of the interface thermal resistance of the surface of the substrate.

2. The method according to claim 1, wherein the determining the data representative of the interface thermal resistance of the surface of the substrate may be performed for a plurality of temperatures, and wherein deriving the bioparticle retention time from the data representative of the interface thermal resistance of the surface of the substrate comprises determining bioparticle retention time and/or detachment rate as function of temperature.

3. The method according to claim 1, wherein determining the data representative of the interface thermal resistance of the surface of the substrate comprises providing a heating power using a power at a first side of the substrate; and sensing at least a temperature at the first side of the substrate and at a second side, opposite to the first side with respect to the substrate.

4. The method according to claim 1, the method further comprising obtaining a substrate having a surface comprising a plurality of binding sites cavities in which a target bioparticle can be bound.

5. The method according to claim 4, wherein the method further comprises providing a sample fluid in contact with the surface comprising the plurality of binding sites and/or wherein the obtaining a substrate comprises binding target bioparticles to the surface comprising the plurality of binding sites.

6. The method according to claim 1, the method further comprising, prior to the determining and the deriving, rinsing the substrate with a fluid.

7. The method according to claim 1, the method further comprising deriving a characteristic of the bioparticle from the bioparticle retention time and/or detachment rate as a function of temperature.

8. A controller programmed for performing a method according to claim 1.

9. A computer program product comprising instructions which, when executed on a processor, induce a method according to claim 1.

10. A bio-sensing device suitable for detection and/or characterization of target bioparticles, the bio-sensing device comprising:
    a heating element for heating using a power;
    a sample holder comprising a substrate having a surface comprising a plurality of binding sites to which target bioparticles can bind, the sample holder further being adapted for exposing the substrate at one side to the heating element;
    a first temperature sensing element for sensing a temperature at the side where the substrate can be exposed to the heating element and a second temperature sensing element for sensing a temperature at the side opposite thereto with respect to the substrate; and
    a processor programmed for determining, for at least one temperature, data representative of thermal resistance data based on temperature values obtained with the first temperature sensing element and the second temperature sensing element and the power for the heating element,
    wherein the processor is programmed for deriving, for at least the one temperature, a bioparticle retention time and/or detachment rate from the data representative of the thermal resistance data.

11. The bio-sensing device according to claim 10, wherein the processor is programmed for calculating the data representative of the thermal resistance data as function of temperature and for deriving bioparticle retention time as function of temperature.

12. The bio-sensing device according to claim 10, wherein the substrate is an imprinted substrate.

13. The bio-sensing device according to claim 10, wherein the substrate is a structured substrate.

14. The bio-sensing device according to claim 10, wherein the substrate is a polymer.

15. The bio-sensing device according to claim 10, wherein the bio-sensing device is adapted for characterizing target bioparticles with an average diameter of D, and wherein the binding sites in the substrate have an average diameter in a range 1.5 times D to 0.5 times D.

16. The bio-sensing device according to claim 10, wherein the binding sites have an average diameter of 0.1 nm to 100 μm.

17. The bio-sensing device according to claim 10, further comprising a fluid compartment.

18. The bio-sensing device according to claim 10, wherein the processor is adapted for outputting, based on the bioparticle retention time and/or detachment rate, a characteristic of target bioparticles.

19. A controller for controlling a bio-sensing device according to claim 10.

20. A diagnostic device comprising a bio-sensing device according to claim 10, the diagnostic device furthermore adapted for deriving based on a characterization of a bioparticle pathology of an object.

* * * * *